United States Patent [19]

Ishibe

[11] 4,319,059

[45] Mar. 9, 1982

[54] PREPARATION OF NITROALKANES

[75] Inventor: Nobuyuki Ishibe, Lake Jackson, Tex.

[73] Assignee: The Dow Chemical Company, Midland, Mich.

[21] Appl. No.: 153,360

[22] Filed: May 27, 1980

[51] Int. Cl.$^3$ .................... C07C 76/02; C07C 79/04
[52] U.S. Cl. .................................... 568/947; 568/948
[58] Field of Search ....................... 568/943, 947, 948

[56] References Cited

U.S. PATENT DOCUMENTS 2,117,931  5/1938  Allen ................................. 568/948
3,014,972  12/1961  Hardies ............................. 568/947
3,038,015  6/1962  Kornblum ........................... 568/947

OTHER PUBLICATIONS

Martin Stiles, "Carboxylation and Alkylation of Nitroparaffins and Ketones, Properties of α-Nitro Acids, Abstracts of Papers, 136th Meeting American Chemical Society, pp. 42p–43p, Sep. 1959.

Stiles, M. and Finkbeiner, H. L., "Chelation as a Driving Force in Synthesis", Journal of the Am. Chem. Soc., vol. 81, p. 506 (1959).

*Primary Examiner*—Paul R. Michl
*Attorney, Agent, or Firm*—A. C. Ancona

[57] ABSTRACT

A process for making nitroalkanes in which an alpha-bromoalkanoic acid is reacted with an alkali metal nitrite, e.g. $NaNO_2$, in the presence of the magnesium ion ($Mg^{++}$) in an aprotic solvent to form a chelate. Neutralization of the chelate with a mineral acid produces a nitroalkane having one less carbon atom than the reactant bromoalkanoic acid.

9 Claims, No Drawings

PREPARATION OF NITROALKANES

BACKGROUND OF THE INVENTION

Nitroalkanes are an essential stabilizing ingredient employed in 1,1,1-trichloroethane when it is used in vapor degreasing and cold cleaning. All manufacturers throughout the world add nitromethane and/or nitroethane to their commercial 1,1,1,-trichloroethane-based solvents. Normally nitro-paraffins are manufactured by a vapor phase nitration of the alkane with either nitric acid or $NO_2$. There is a mixture of products formed due to carbon-carbon scission. Thus, for example, when propane is nitrated, the products include 1-nitropropane, 2-nitropropane, nitroethane and nitromethane. Because of the oxidative conditions other oxygen containing compounds are also produced, eg. aldehydes, acids and carbon oxides.

It would be advantageous to have a process which provided a purer product and was less extravagant in its use of energy than the known vapor phase process.

It has now been found that an alpha-bromoalkanoic acid can be reacted with an alkali metal nitrite in the presence of the magnesium ion in an aprotic solvent to form a chelate which upon treatment with a mineral acid yields a nitroalkane of one less carbon atom than the reactant bromoacid.

SUMMARY OF THE INVENTION

An α-bromoalkanoic acid, e.g., α-bromopropionic acid, is reacted with an alkali metal nitrite, e.g., $NaNO_2$ in the presence of $Mg^{++}$ ion provided by adding a magnesium salt, e.g., $MgSO_4$, to the mixture, all in a solution of an aprotic solvent, e.g., dimethyl sulfoxide. This mixture is allowed to react with stirring at room temperature and then neutralized with a mineral acid, e.g., HCl. The product is a nitroalkane, which in the case of starting with α-bromopropionic acid is nitroethane.

DETAILED DESCRIPTION OF THE INVENTION

Without attempting to describe the mechanism, the following equation shows the reaction:

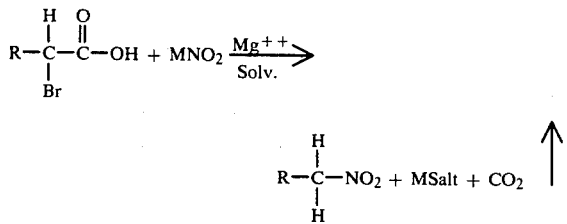

wherein M is an alkali metal R is H or an alkyl group of 1-4 carbon atoms and the solvent is aprotic. After reacting the mixture it is neutralized with a mineral acid.

Thus, an α-bromoalkanoic acid reacted with an alkali metal nitrite in the presence of $Mg^{++}$ ion in an aprotic solvent will yield a nitroalkane having one less carbon atom than the starting bromo-alkanoic acid. The alkali metal is converted to the salt of the mineral acid used to neutralize the mixture.

The α-bromo acids useful in the process are, for example bromoalkanoic acids having from 2 to 6 carbon atoms. Thus, α-bromoacetic, α-bromopropionic, α-bromobutanoic, αbromopentanoic and the like acids maybe employed.

Alkali metal nitrites useful in the process are sodium and potassium nitrites. It is believed that the function of the magnesium ion is to form a chelate intermediate

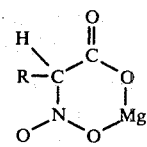

which can then be decomposed by the addition of a mineral acid, decarboxylating the alkanoic acid moiety. Ionizable magnesium compounds useful in the process are magnesium alkoxides, such as magnesium methoxide, magnesium sulfate, magnesium chloride or bromide.

Both the magnesium compound and the nitrite are employed in a molar equivalent amount based on the moles of bromo acid used. In order to insure complete reaction of the halo acid a slight excess of each of these is employed. The reaction to form the chelate is considered complete upon the substantial disappearance of the nitrite, i.e., the amount equivalent to the bromoacid.

Aprotic solvents employed are selected from amides and sulfoxides, e.g., dimethyl formamide and dimethyl sulfoxide.

The following examples are illustrative of the invention:

EXAMPLE 1

To a mixture of magnesium methoxide (0.11 mole) and dimethyl sulfoxide (50 ml) α-bromopropionic acid (0.11 mole) ws added at 20° C. with stirring. To this mixture a solution of sodium nitrite (0.145 mole) in dimethyl sulfoxide (65 ml) was added at room temperature. Then, the reaction mixture was stirred at room temperature for 6 hours and was neutralized upon addition of diluted hydrochloric acid. The product was analyzed on a 3'×3/16" Porapak Q column for nitroethane at 150° C. and on a 3'×3/16" column packed with 10% ethylene glycol adipate and 1% phosphoric acid on Chromosorb AW 80/100 mesh for α-bromopropionic acid at 150° C. This analysis of the reaction mixture indicated more than 99% conversion of α-bromopropionic acid and 94.5% yield of nitroethane.

EXAMPLE 2

In the manner of Example 1 sodium nitrite, α-bromopropionic acid and magnesium methoxide were reacted in dimethyl sulfoxide as the aprotic solvent. The reaction time was 2 hours for one run and 22 hours for another. Reaction was conducted at room temperature. The run at 2 hours converted only 94.5% of the acid and yielded 72.7% nitroethane. The second run at 22 hours gave a conversion of >99% and a yield of 100%.

At room temperature the reaction apparently takes about 4-5 hours to go to completion. At higher temperatures of 40° C. up to about 75° C. the reaction time is shorter. Thus, one or two hours or even less time at 75° C. will completely convert the bromoacid to the intermediate which can then be decomposed to the nitroalkane.

When using dimethyl sulfoxide as solvent temperatures approaching 100° C. should be avoided since the solvent will volatilize and decompose at about 100° C. Other aprotic solvents may not have this disadvantage.

I claim:

1. A process for making a nitroalkane which comprises reacting an α-bromoalkanoic acid with an alkali metal nitrite in the presence of magnesium ions in an aprotic solvent for a time sufficient to form a cyclic chelate intermediate and thereafter neutralized with a mineral acid thereby to decarboxylate the alkanoic acid moiety in said chelate intermediate to obtain the nitroalkane.

2. The process of claim 1 wherein the α-bromoalkanoic acid contains from 2 to 6 carbon atoms.

3. The process of claim 2 wherein the alkali metal nitrite is sodium or potassium nitrite.

4. The process of claim 1 wherein the magnesium ions are provided by an ionizable magnesium compound.

5. The process of claim 4 wherein the ionizable magnesium compound is selected from magnesium alkoxides, sulfates, chlorides or bromides.

6. The process of claim 2 wherein the α-bromoalkanoic acid is α-bromo substituted acetic, propionic, butanoic or pentanoic acid.

7. The process of claim 1 wherein the aprotic solvent is dimethyl formamide or dimethyl sulfoxide.

8. The process of claim 1 wherein the mineral acid employed is hydrochloric acid.

9. The process of claim 1 wherein the α-bromoalkanoic acid is α-bromopropionic, the alkali metal nitrite is sodium nitrite, the magnesium compound is magnesium methoxide, the aprotic solvent is dimethyl sulfoxide and the mineral acid is hydrochloric acid.

* * * * *